United States Patent
Kosugi (10) Patent No.: US 10,159,458 B2
(45) Date of Patent: Dec. 25, 2018

(54) X-RAY DIAGNOSTIC APPARATUS

(71) Applicant: TOSHIBA MEDICAL SYSTEMS CORPORATION, Otawara-Shi (JP)

(72) Inventor: Norimitsu Kosugi, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/810,894

(22) Filed: Jul. 28, 2015

(65) Prior Publication Data

US 2016/0038115 A1 Feb. 11, 2016

(30) Foreign Application Priority Data

Aug. 7, 2014 (JP) ................. 2014-161741

(51) Int. Cl.
*A61B 6/00* (2006.01)
*A61B 6/04* (2006.01)

(52) U.S. Cl.
CPC ............ *A61B 6/547* (2013.01); *A61B 6/0457* (2013.01)

(58) Field of Classification Search
CPC ....... A61B 6/04; A61B 6/0457; A61B 6/0407; A61B 6/0442; A61B 5/0555; A61B 6/0421; A61B 6/0414; A61B 6/0435; A61B 5/704; A61B 6/0428; A61N 2005/1097; A61G 13/00; A61G 13/02
See application file for complete search history.

(56) References Cited

U.S. PATENT DOCUMENTS

| | | | |
|---|---|---|---|
| 5,926,002 A * | 7/1999 | Cavanaugh | A47C 31/008 297/284.3 |
| 2007/0101500 A1* | 5/2007 | Fruh | A61G 13/02 5/613 |

FOREIGN PATENT DOCUMENTS

JP  2010-104492  5/2010

* cited by examiner

*Primary Examiner* — Hoon Song
(74) *Attorney, Agent, or Firm* — Oblon, McClelland, Maier & Neustadt, L.L.P.

(57) ABSTRACT

An X-ray diagnostic apparatus according to an embodiment includes a bed that has a top board on which an object is placed, a console configured to manipulate an actuation of the bed in an inverting direction, in which the object is inclined to locate a head lower than a foot, and an actuation of the bed in a raising direction, in which the object is inclined to locate the head higher than the foot, and a processing circuitry configured to receive an input from the console and control an actuation of the bed, and the processing circuitry determines whether the head of the object is located closer to one shorter side of the bed or to another shorter side of the bed, and changes a control of an actuation of the bed programmed in the console based on a result of the determination.

10 Claims, 8 Drawing Sheets

X-RAY DIAGNOSTIC APPARATUS

CROSS-REFERENCE TO RELATED APPLICATION

This application is based upon and claims the benefit of priority from Japanese Patent Application No. 2014-161741, filed on Aug. 7, 2014, the entire contents of which are incorporated herein by reference.

FIELD

An embodiment, which is an aspect of the present invention, relates to an X-ray diagnostic apparatus.

BACKGROUND

An X-ray diagnostic apparatus is a modality apparatus that irradiates an object with X-rays and detects the amount of X-rays transmitted through the object, thereby enabling less invasive observation of an internal structure of the object. The amount of X-rays transmitted through the object differs between tissues of the body of the object, and the difference enables imaging of different tissues. Using a contrast medium in imaging enables real-time observation of) how various tissues or organs, such as the blood flow, the alimentary canal or the urinary system, are working, and the X-ray diagnostic apparatus is widely used for diagnosis of diseases and surgery.

For example, in stomach examination by imaging performed in medical checkup, the bed on which the object is placed is raised and inverted to allow the gastric wall to be coated with the contrast medium. The bed raising and inverting operations include inclination of the bed in a direction to raise the head of the object (raising direction) and inclination of the bed in a direction to lower the head of the object (inverting direction). In the following, the inclination of the bed in the direction of inverting the object will be referred to as reverse inclination. Such bed raising and inverting operations are achieved by operating a bed actuation lever on a console installed in a manipulation room or the like. When the bed is reversely inclined, taking into consideration the risk of the object falling off the bed, a double-action operation is adopted which involves an operation of permitting reverse inclination in addition to the operation of actuating the bed.

However, it can be difficult for an operator in the manipulation room to observe the object placed on the bed in the examination room because of the layout of the manipulation room and the examination room. In such a case, the object needs to be placed on the bed in a reverse orientation (reverse position) to the normal orientation. If the object is placed in the reverse position, the reverse inclination of the bed can be achieved in a single-action operation that involves only the operation of actuating the bed, and the single-action operation can be accidentally performed.

In view of this, there has been provided an X-ray diagnostic apparatus that can reverse the setting of the bed actuation operation when the apparatus is installed depending on the layout of the manipulation room and the examination room.

However, whether or not the object is placed in the reverse orientation (reverse position) to the normal orientation depends not only on the layout of the manipulation room and the examination room but also on the type of the examination or the part to be examined. In particular, with the X-ray diagnostic apparatus used for various examinations or surgeries, the position of the object placed on the bed needs to be arbitrarily chosen.

For example, in endoscopic retrograde cholangiopancreatography (ERCP), a bile duct or a pancreatic duct is imaged while inserting an endoscope for examination or surgery. Therefore, the practitioner needs to stand around the bed, or the endoscopic system or other instruments need to be disposed around the bed, so that the orientation of the object placed on the bed needs to be chosen depending on the layout of the instruments and the like.

In addition, the imaging position differs between when an abdomen or foot is imaged and when a chest or a head is imaged. Therefore, the orientation of the object placed on the bed needs to be changed depending on the part to be imaged. In addition, the range of movement of the bed in the bed raising and inverting operations can differ between when the bed is inclined and when the bed is reversely inclined, so that the orientation of the object needs to be chosen depending on the part to be imaged.

Furthermore, the bed actuation may be performed using a manipulation panel installed in the manipulation room or using a mobile console. In particular, in the case of using the mobile console, the raising and inverting operations need to be independent of the layout of the console.

According to a prior art invention, the bed raising and inverting operations are performed according to a previously determined setting, regardless of the orientation of the object. Therefore, the reverse inclination can be able to be achieved only by the operation of actuating the bed (referred to as a single-action operation, hereinafter). In addition, whether only the operation of actuating the bed is required or an operation of permitting the reverse inclination is required in addition to the operation of actuating the bed may be considered before actuating the bed.

As described above, even when the object is placed on the bed in the reverse orientation (reverse position) to the normal orientation, the reverse inclination of the bed in the direction of lowering the head of the object needs to be achieved by two operations, that is, the operation of actuating the bed and the operation of permitting the reverse inclination (referred to as a double-action operation, hereinafter). In addition, when the orientation of the object is changed, whether to use the double-action operation or the single-action operation needs to be chosen depending on the orientation of the object.

Thus, there is a demand for an X-ray diagnostic apparatus that can be operated independently of the orientation of an object placed on a bed.

DETAILED DESCRIPTION

In the following, an X-ray diagnostic apparatus according to an embodiment will be described with reference to the accompanying drawings.

The X-ray diagnostic apparatus according to this embodiment comprises a bed that has a top board on which an object is placed, a console configured to manipulate an actuation of the bed in an inverting direction, in which the object is inclined to locate a head lower than a foot, and an actuation of the bed in a raising direction, in which the object is inclined to locate the head higher than the foot, and a processing circuitry configured to receive an input from the console and control an actuations of the bed. The processing circuitry determines whether the head of the object is located closer to one shorter side of the bed or to another shorter side of the bed, and changes a control of an actuation of the bed programmed in the console based on a result of the determination.

(1) Configuration

Figure 1:
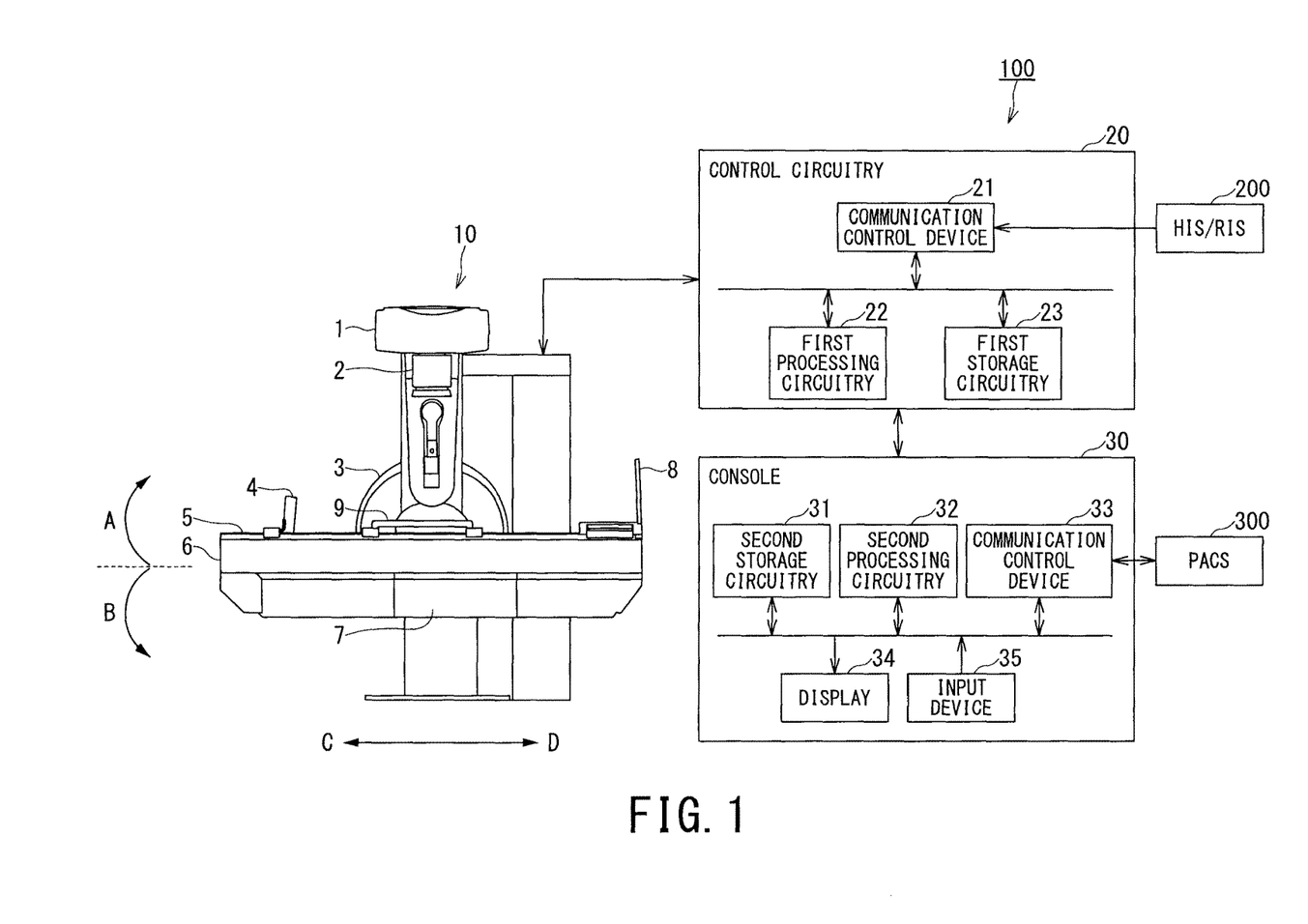
FIG. 1 is a conceptual diagram showing an example of an X-ray diagnostic apparatus according to an embodiment.

FIG. 1 is a conceptual diagram showing an example of an X-ray diagnostic apparatus 100 according to this embodiment. As shown in FIG. 1, the X-ray diagnostic apparatus 100 comprises an X-ray imaging device 10, a control circuitry 20, and a console 30.

First, the X-ray imaging device 10 will be described. The X-ray imaging device 10 has an imaging unit (imaging device) 1, a variable X-ray aperture 2, a bed raising/inverting unit 3, a shoulder rest 4, a top board 5, a bed 6, an X-ray detecting unit 7, a foot rest 8, and a side hand grip 9.

The imaging unit 1 comprises an X-ray tube that produces X-rays, and the X-ray tube produces X-rays when a voltage from a high voltage power supply is applied thereto under the control of the control circuitry 20.

The variable X-ray aperture 2 adjusts the range of irradiation with the X-rays applied by the imaging unit 1 on the object placed on the top board 5. The variable X-ray aperture 2 can reduce the radiation dose of the object.

The X-ray detecting unit 7 is placed at a position opposed to the imaging unit 1. As shown in FIG. 1, the X-ray detecting unit 7 is provided in the bed 6 and detects the X-rays transmitted through the object. The X-ray detecting unit 7 is constituted by an image intensifier that converts the X-rays transmitted through the object into an optical image. As an alternative to the image intensifier, a flat panel detector may be used. Furthermore, the X-ray detecting unit 7 responsible for fluoroscopic imaging may be provided with an X-ray "TV" camera. Detection data obtained by the X-ray detecting unit 7 is transmitted to the console 30.

The bed 6 is provided on top thereof with the top board 5 on which the object is placed. Under the control of the control circuitry 20, the bed raising/inverting unit 3 raises or inverts the bed 6. The bed 6 rotates about the bed raising/inverting unit 3. Raising and inverting operations of the bed 6 include a normal rotation, which is a clockwise rotation with the top surface of the bed facing forward (in the direction indicated by the arrow A in FIG. 1), and a reverse rotation, which is a counterclockwise rotation (in the direction indicated by the arrow B in FIG. 1). For example, if the object is placed on the bed with the head located on the side C of the bed, the bed is inclined in a direction to raise the head of the object (raising direction) as the bed rotates in the direction indicated by the arrow A in FIG. 1. On the other hand, the bed is inclined in a direction to lower the head of the object (inverting direction) as the bed rotates in the direction indicated by the arrow B. In the following, the rotation in the direction of the arrow A will be referred to as a normal rotation, and the rotation in the direction of the arrow B will be referred to as a reverse rotation. The operation of inclining the bed on which the object is placed in the raising direction will be referred to simply as "inclination", and the operation of inclining the bed in the direction to invert the object will be referred to as "reverse inclination".

The shoulder rest 4, the foot rest 8 and the side hand grip 9 are provided to prevent the object from falling off the bed. The shoulder rest 4 prevents the object from falling off the bed when the bed 6 is reversely inclined, and the foot rest 8 prevents the object from falling off when the bed 6 is inclined. The shoulder rest 4 and the foot rest 8 are configured to be able to be easily removed. For example, the object may be placed on the bed with the head located on the side C in FIG. 1 (referred to as a normal position, hereinafter) or placed on the bed with the head located on the side D (referred to as a reverse position, hereinafter). In the normal position, the shoulder rest 4 is attached to the bed 6 on the side C where the head of the object is located, and the foot rest 8 is attached to the bed 6 on the side D where the feet of the object are located. On the other hand, in the reverse position, the shoulder rest 4 is attached to the bed 6 on the side D where the head of the object is located, and the foot rest 8 is attached to the bed 6 on the side C where the feet of the object are located. In this way, the shoulder rest 4 and the foot rest 8 are removable and can be easily interchanged.

The control circuitry 20 controls the X-ray imaging device 10 and the console 30 and also controls the whole of the X-ray diagnostic apparatus 100. The control circuitry 20 comprises a communication control device 21, a first processing circuitry 22, and a first storage circuitry 23. The control circuitry 20 is connected to a hospital information system/radiology information system (HIS/RIS) 200 via the communication control device 21. The HIS/RIS 200 is an ordering system that processes an examination request from a doctor or the like via an electronic network.

The communication control device 21 includes various communication protocols for different forms of networks. The term "electronic network" used herein means an entire information communication network based on a telecommunication technique, and examples of the electronic network includes a hospital backbone LAN, a wireless/wired LAN and the Internet as well as a telephone network, an optical fiber communication network, a cable communication network and a satellite communication network.

The first processing circuitry 22 is a processor that reads a program from the first storage circuitry 23 and executes the program to implement a function corresponding to the program. In other words, the first processing circuitry 22 (processor) can read a program and implement a function described later.

The first storage circuitry 23 stores various programs. The programs stored in the first storage circuitry 23 are executed by the first processing circuitry 22, thereby achieving the bed raising/inverting control, the imaging control and the like.

The first storage circuitry 23 is constituted by a storage medium or the like, such as a RAM or a ROM, and includes a storage medium readable by the first processing circuitry 22, such as a magnetic or optical storage medium or a semiconductor memory. Some or all of the programs and data in the storage medium may be downloaded via the electronic network.

The console 30 makes each part of the bed actuate in response to an image display or an input for bed raising and inverting operations based on X-ray transmission data obtained by the X-ray imaging device 10. The console 30 comprises a second storage circuitry 31, a second processing circuitry 32, a communication control device 33, a display 34, and an input device 35. The console 30 is connected to a picture archiving and communication systems (PACS) 300 via the communication control device 33 and the electronic network. The PACS 300 is a server that accumulates obtained medical images. An X-ray image taken by the X-ray imaging device 10 is accumulated in the PACS 300. The console 30 may obtain an X-ray image via the PACS 300, via the control circuitry 20 or directly from the X-ray imaging device 10.

The second storage circuitry 31 stores an X-ray image or a program. A program stored in the second storage circuitry 31 is executed by the second processing circuitry 32 to change the display orientation of the image shown on the display 34. For the imaging site input via the input device 35, similarly, the display orientation of the image is changed depending on the examination mode.

As with the first storage circuitry 23, the second storage circuitry 31 is constituted by a storage medium or the like, such as a RAM or a ROM, and includes a storage medium readable by the second processing circuitry 32, such as a magnetic or optical storage medium or a semiconductor memory. Some or all of the programs and data in the storage medium may be downloaded via the electronic network.

The second processing circuitry 32 is a processor that reads a program from the second storage circuitry 31 and executes the program to implement a function corresponding to the program. In other words, the second processing circuitry 32 (processor) can read a program and implement a function of changing the display orientation of the image.

As with the communication control device 21 of the control circuitry 20, the communication control device 33 includes various communication protocols for different forms of networks.

In the console 30, the second processing circuitry 32 executes a program stored in the second storage circuitry 31 to achieve display of an X-ray image, input of the imaging orientation or the like.

The display 34 is constituted by a common display device, such as a liquid crystal display or an organic light emitting diode (OLED) display, and provides display of an X-ray image under the control of the second processing circuitry 32.

The input device 35 is constituted by a common input device, such as a keyboard, a touch panel, a ten-key or a mouse. The input device 35 outputs, to the second processing circuitry 32, an input signal responsive to a user operation, such as input of the imaging site or choice of the examination mode.

Figure 2:
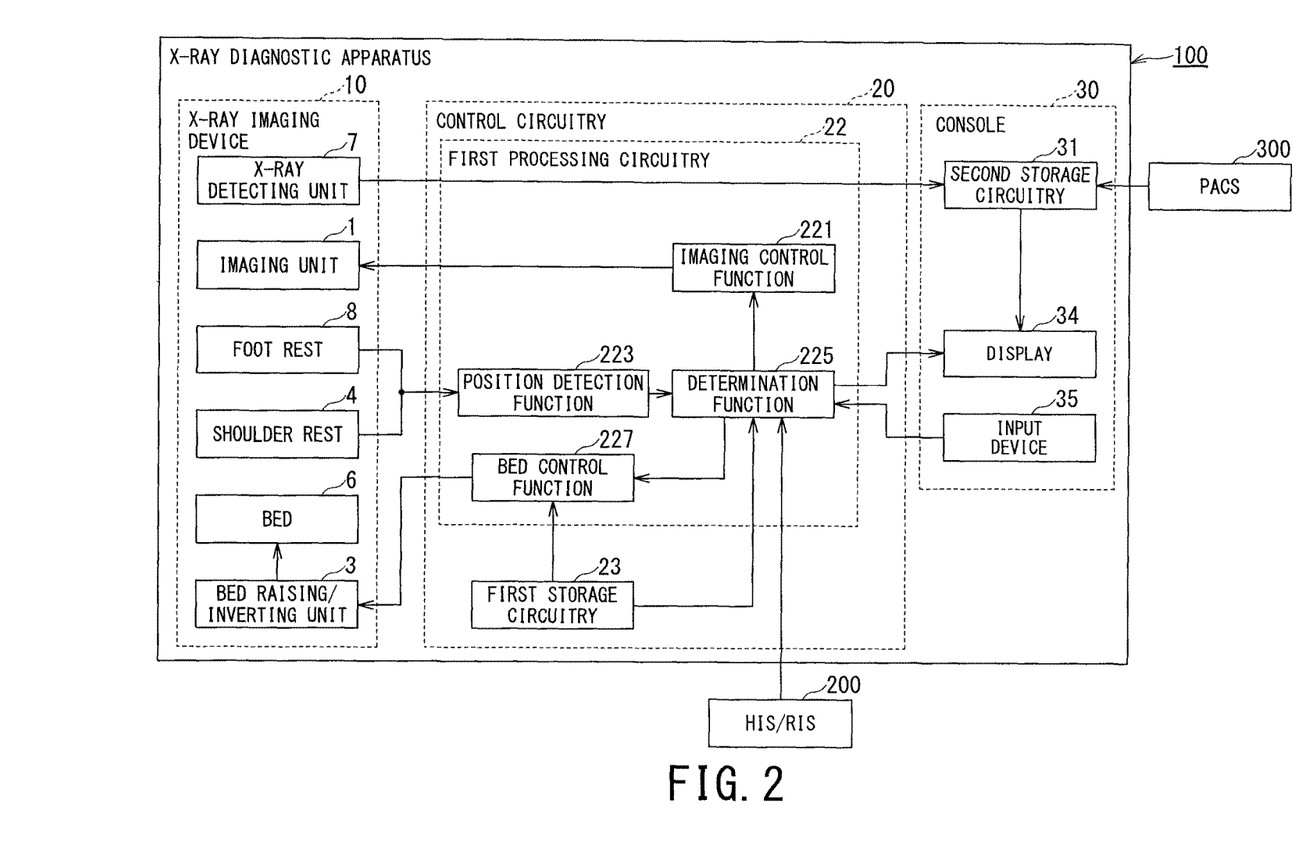
FIG. 2 is a functional block diagram showing an example of a functional configuration of the X-ray diagnostic apparatus according to the embodiment.

FIG. 2 is a functional block diagram showing an example of a functional configuration of the X-ray diagnostic apparatus 100 according to this embodiment. As also shown in FIG. 1, the X-ray diagnostic apparatus 100 comprises the X-ray imaging device 10, the control circuitry 20, and the console 30.

As shown in FIG. 2, the control circuitry 20 of the X-ray diagnostic apparatus 100 has an imaging control function 221, a position detection function 223, a determination function 225, a bed control function 227, and the first storage circuitry 23. Of these components, the imaging control function 221, the position detection function 223, the determination function 225 and the bed control function 227 are functions implemented by the first processing circuitry 22 executing a relevant program stored in the first storage circuitry 23.

That is, the first processing circuitry 22 is a processor that reads a relevant program from the first storage circuitry 23 and executes the program to implement a function corresponding to the program. In other words, the first processing circuitry 22 (processor) can implement the imaging control function 221, the position detection function 223, the determination function 225 and the bed control function 227 by reading the respective corresponding programs.

The position detection function 223 detects a position of attachment of the shoulder rest 4 and the foot rest 8 of the X-ray imaging device 10.

The determination function 225 determines whether the head of the object is located closer to one shorter side of the bed 6 or located closer to another shorter side of the bed 6. That is, the determination function 225 determines whether the examination mode is a normal position mode in which the head of the object is located closer to one shorter side of the bed 6 or a reverse position mode in which the head of the object is located closer to another shorter side of the bed. For example, with the bed 6 of the X-ray imaging device 10 shown in FIG. 1, if a mode in which the head of the object is located on the side C is defined as the normal position mode, a mode in which the object is placed on the bed in the position opposite to the normal position is defined as the reverse position mode. Alternatively, a position mode initially set at the time of installation of the bed may be defined as the normal position mode, and a position mode in which the object is placed in the opposite position may be defined as the reverse position mode. The following description will be made on the assumption that the mode in which the head of the object is located on the side C in FIG. 1 is the normal position mode.

The determination function 225 determines whether the examination mode is the normal position mode or the reverse position mode based on at least one of the position of the foot rest 8 attached to the bed, the position of the shoulder rest 4 attached to the bed, the type of the examination, and the part to be examined. The method of determining the examination mode will be described later.

Based on the result of the determination, the bed control function 227 changes the control of the actuation of the bed 6 programmed in the console 30. That is, the bed control function 227 changes the control of the bed 6 programmed in the console 30 in response to the examination mode. The bed 6 can be actuated in a normal rotation direction in which the bed 6 rotates clockwise with the top surface facing forward (the direction of the arrow A shown in FIG. 1) or in a reverse rotation direction in which the bed 6 rotates counterclockwise (the direction of the arrow B shown in FIG. 1).

If the examination mode is the normal position mode, the first processing circuitry 22 performs a control to set an actuation operation on the console 30 to be a single-action operation, and if the examination mode is the reverse position mode, the first processing circuitry 22 performs a control to set the actuation operation on the console 30 to be a double-action operation. That is, if the examination mode is the normal position mode, the normal rotation is achieved in a single-action operation that involves only an operation of actuating the bed, and the reverse rotation is achieved in a double-action operation that involves two operations: an operation of actuating the bed, and an operation of permitting the reverse rotation. If the examination mode is the reverse position mode, the control performed is reverse to that performed in the normal position mode: the normal rotation is achieved in a double-action operation, and the reverse rotation is achieved in a single-action operation. With such a control, the object placed on the bed 6 can be inclined in the raising direction in the single-action operation, and can be reversely inclined in the inverting direction in the double-action operation. A control of the bed by the bed control function 227 will be described later.

The first storage circuitry 23 stores settings of movement of the bed 6, such as a range of movement of the bed 6, a horizontal rest position of the bed 6, and a speed of movement of the bed 6. The range of movement of the bed 6 is determined by a limit position of movement of the bed 6 in the raising direction and a limit position of movement of the bed 6 in the inverting direction. The range of movement of the bed 6 and the horizontal rest position of the bed 6 will be described later.

The imaging control function 221 performs a control of a movement of the imaging unit 1. The imaging control function 221 changes the control of the movement of the imaging unit 1 programmed in the input device 35 in response to the examination mode.

The console 30 of the X-ray diagnostic apparatus 100 has, the second storage circuitry 31, the display 34 and the input device 35.

The second storage circuitry 31 stores an X-ray image obtained by the X-ray imaging device 10 or an X-ray image obtained from the PACS 300.

The display 34 displays an X-ray image of the object placed on the bed 6 and changes the display orientation to make the side of the head of the object in the X-ray image agree with the upper side of the display 34 based on the examination mode. The display 34 displays the examination mode determined by the determination function 225. The display orientation of the X-ray image and the change of the display orientation will be described later.

The input device 35 accepts an input of the direction of movement of the imaging unit 1 that images the object. In addition, the examination mode and examination information are input to the input device 35 by the user, such as a doctor or an examination technician.

(2) Operation

In the following, an operation of the X-ray diagnostic apparatus 100 according to this embodiment will be described. First, a problem with the bed raising and inverting operations of a conventional X-ray diagnostic apparatus will be described.

Figure 3A:
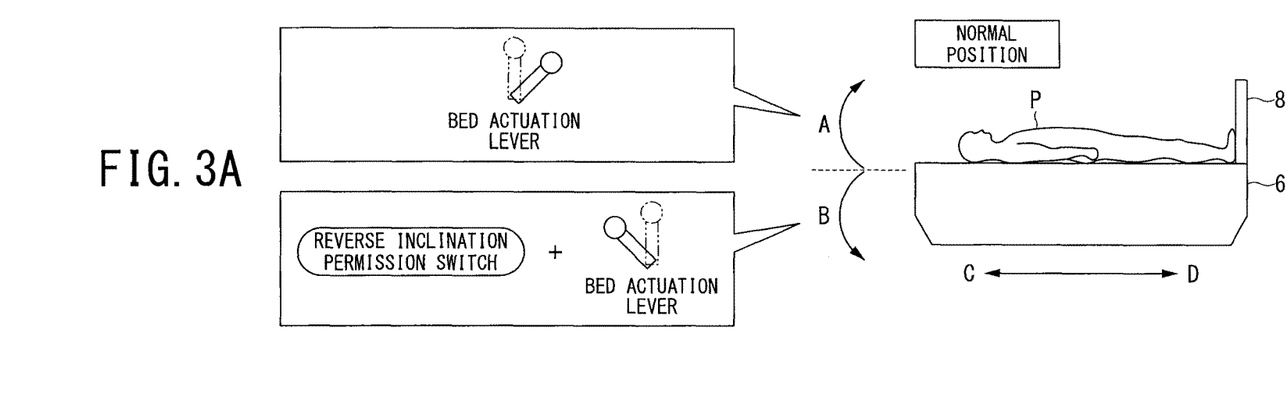
FIG. 3A is a diagram for illustrating raising and inverting operations of a conventional X-ray diagnostic apparatus in a normal position mode.
Figure 3B:
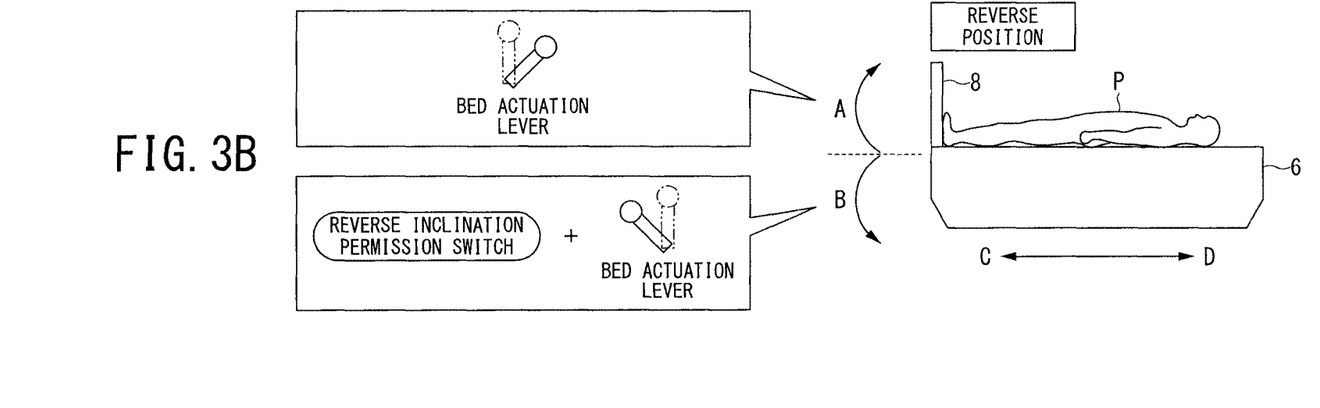
FIG. 3B is a diagram for illustrating raising and inverting operations of the conventional X-ray diagnostic apparatus in a reverse position mode.

FIGS. 3A and 3B are diagrams for illustrating raising and inverting operations of a conventional X-ray diagnostic apparatus in the normal position mode and the reverse position mode. FIG. 3A shows a case where an object P is placed facing up on a bed with the head located on the side C (normal position), and FIG. 3B shows a case where the object P is placed facing up on the bed with the head located on the side D (reverse position).

With the conventional X-ray diagnostic apparatus 100, the bed raising and inverting operations are previously programmed in the console 30 or the input device 35, and a required manipulation is set for each operation. For example, the upper left part of FIG. 3A shows an operation of inclining the bed in the direction of the arrow A (that is, the normal rotation), and the lower left part of FIG. 3A shows an operation of inclining the bed in the direction of the arrow B (that is, the reverse rotation). The operation shown in the upper left part of FIG. 3A involves only an operation of a bed actuation lever (that is, a single-action operation). On the other hand, the operation shown in the lower left part of FIG. 3A is a double-action operation. The double-action operation is an operation that involves an operation of the bed actuation lever and an operation of pressing a switch (referred to as a reverse inclination permission switch, hereinafter) to permit the reverse inclination. The operation shown in the lower left part of FIG. 3A corresponds to the bed actuation in the direction of the arrow B shown in the right part of FIG. 3A and causes reverse rotation of the bed 6 on which the object P is placed. As shown in FIG. 3A, as the bed rotates in the direction of the arrow B, the object is inclined in the inverting direction. When the bed is inclined in the inverting direction, the object P would otherwise be extremely highly likely to fall headlong off the bed, so that the double-action operation is adopted in order to prevent the bed from being accidentally actuated.

With the conventional X-ray diagnostic apparatus, however, the object P can be placed on the bed in the reverse orientation to the orientation shown in FIG. 3A as shown in FIG. 3B. That is, the object P can be placed in the reverse orientation where the head is located on the side D for examination. Even in such a case, the setting of the bed raising and inverting operations is the same as that shown in the left part of FIG. 3A. Thus, the same operation as that shown in the upper left part of FIG. 3A causes inclination of the object P placed on the bed in the reverse direction. That is, the operation to cause the normal rotation of the bed shown in the upper left part of FIG. 3B causes inclination of the bed 6 in the direction of the arrow A. That is, the object P on the bed 6 is inclined in the inverting direction in a single-action operation. On the other hand, the operation to cause the reverse rotation of the bed shown in the lower left part of FIG. 3B causes inclination of the bed 6 in the direction of the arrow B. That is, the double-action operation is needed to incline the object P on the bed 6 in the raising direction.

As described above, with the conventional X-ray diagnostic apparatus, since the bed raising and inverting operations are previously set, an operation reverse to the previously set operation has to be performed when the object P is placed in an orientation different to the previously set orientation. Furthermore, there is a possibility that the object P on the bed 6 can be inclined in the inverting direction in a single-action operation, so that the bed actuation requires special care. The bed 6 has to be properly actuated under instructions from the doctor or the like who perform the examination, surgery or the like. With the conventional X-ray diagnostic apparatus, when the object P is placed on the bed in an orientation different from the previously set orientation, the operation differs from the normal operation. Therefore, it is difficult to smoothly operate the conventional X-ray diagnostic apparatus.

In order to solve the problem described above, the X-ray diagnostic apparatus 100 according to this embodiment determines the examination mode by detecting the orientation of the object P placed on the bed based on the positions of the shoulder rest 4 and foot rest 8 attached to the bed 6, the type of the examination, or the part to be examined, and controls the bed raising and inverting operations in response to the orientation of the object P placed on the bed.

In the following, an operation of the X-ray diagnostic apparatus 100 according to this embodiment will be described with reference to a flowchart.

Figure 4:
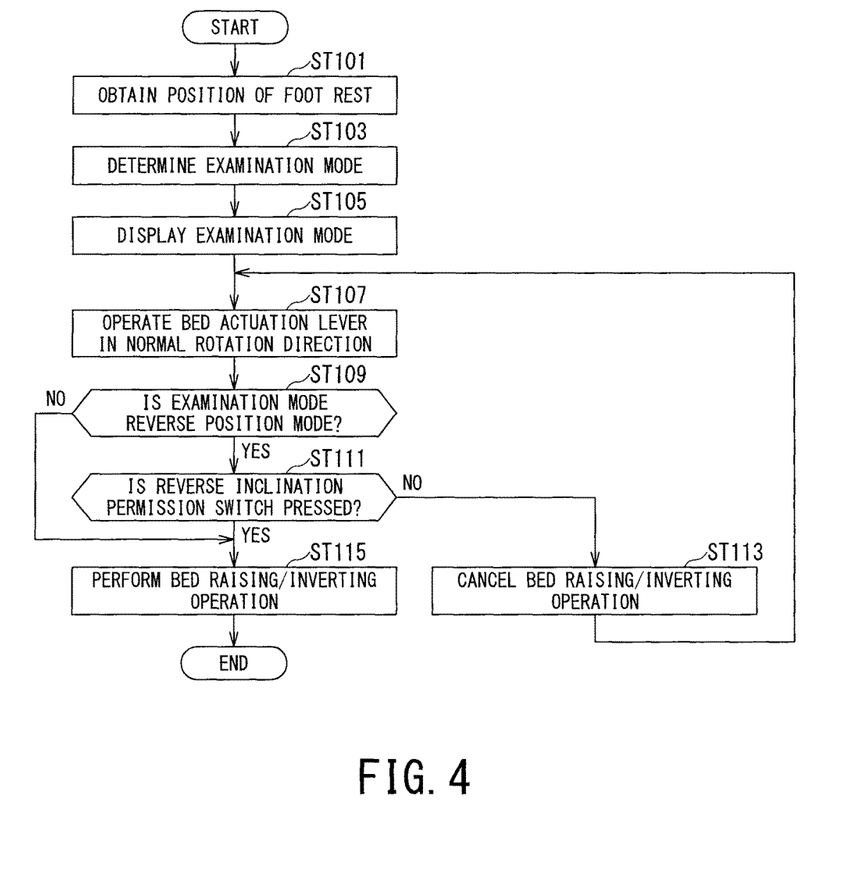
FIG. 4 is a flowchart showing an example of an operation of the X-ray diagnostic apparatus according to the embodiment.

FIG. 4 is a flowchart showing an example of an operation of the X-ray diagnostic apparatus 100 according to this embodiment. Referring to FIG. 4, a case where the examination mode is determined based on the position of the foot rest 8 will be described.

In ST101, the position detection function 223 obtains the position of attachment of the foot rest 8.

In ST103, the determination function 225 determines the examination mode. The determination of the examination mode is made based on the position of the foot rest 8 detected by the position detection function 223, for example. The examination mode may be the normal position mode or the reverse position mode. For example, the determination function 225 determines that the examination mode is the normal position mode if the foot rest 8 is located on the side D in FIG. 1, and determines that the examination mode is the reverse position mode if the foot rest 8 is located on the side C in FIG. 1.

In ST105, the display 34 displays the examination mode determined by the determination function 225. The display of the examination mode allows the user to confirm that the determined examination mode is not an examination mode different from the examination mode intended by the user.

In ST107, the user operates the bed actuation lever of the input device 35. The bed raising and inverting operations are previously programmed in the console 30 or the input device 35, and a required manipulation is set for each operation. In the example shown in FIG. 4 described below, the actuation lever is operated in the normal rotation direction.

In ST109, it is determined whether the examination mode is the reverse position mode or not. If the examination mode is not the reverse position mode, that is, if the examination mode is the normal position mode (if No in ST109), the bed is raised or inverted in ST115. In the normal position mode, an operation of the actuation lever in the normal rotation direction causes inclination of the bed in the direction of inverting the object P, and therefore, the bed can be actuated only in a single-action operation.

On the other hand, if the examination mode is the reverse position mode (if Yes in ST109), it is further determined in ST111 whether the reverse inclination permission switch is pressed or not. In the reverse position mode, an operation of the actuation lever in the normal rotation direction causes inclination of the bed in the direction of inverting the object P, and therefore, a double-action operation is needed that involves operation of the bed actuation lever and pressing of the reverse inclination permission switch.

If the bed control function 227 determines in ST111 that, in the reverse inclination mode, the reverse inclination permission switch is not pressed although the bed actuation lever is operated (if No in ST111), in ST113, the bed control function 227 cancels the bed raising and inverting operations and prevents actuation of the bed. Even in the reverse inclination mode, if not only the bed actuation lever is operated but also the reverse inclination permission switch is pressed (if Yes in ST111), in ST115, the bed control function 227 permits the bed raising and inverting operations. In this way, switching between the operations programmed in the console 30 or the input device 35 occurs in response to the examination mode determined based on the orientation of the object placed on the bed.

Figure 5A:
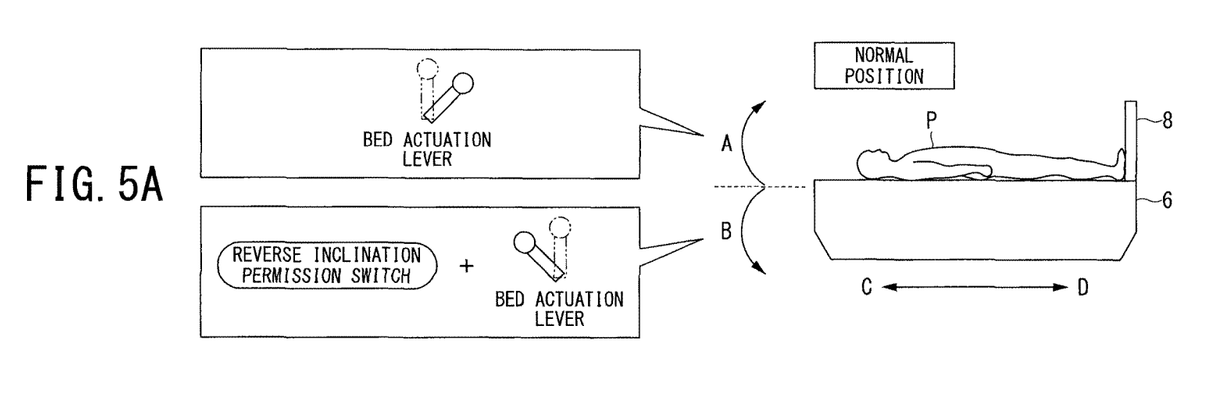
FIG. 5A is a diagram for illustrating the raising and inverting operations of the X-ray diagnostic apparatus according to the embodiment in the normal position mode.
Figure 5B:
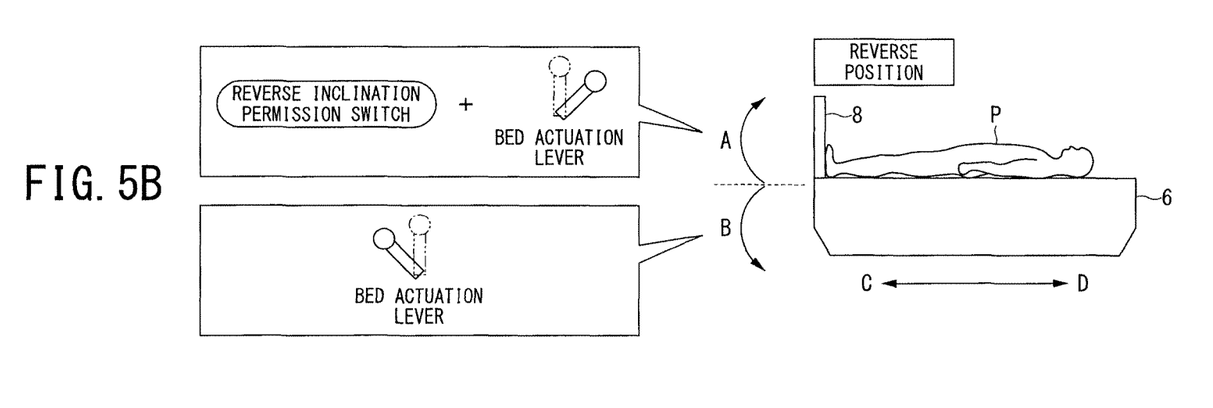
FIG. 5B is a diagram for illustrating the raising and inverting operations of the X-ray diagnostic apparatus according to the embodiment in the reverse position mode.

FIGS. 5A and 5B are diagrams for illustrating the raising and inverting operations of the X-ray diagnostic apparatus 100 according to this embodiment in the normal position mode and the reverse position mode. As with the example shown in FIG. 3, FIG. 5A shows a case where the object P is placed facing up in the normal position orientation, and FIG. 5B shows a case where the object P is placed facing up in the reverse position orientation.

The example shown in FIGS. 5A and 5B differs from the example shown in FIGS. 3A and 3B in that, when the object P is placed in the reverse position orientation, the determination function 225 determines that the examination mode is the reverse position mode based on the position of the foot rest 8, for example. Therefore, as shown in the upper left part of FIG. 5B, even in the reverse position mode, when the bed is to be normally rotated in the direction of the arrow A shown in the right part of FIG. 5B to incline the object P in the inverting direction, the double-action operation is performed that involves operation of the bed actuation lever and pressing the reverse inclination permission switch. On the other hand, when the bed is reversely rotated in the direction of the arrow B shown in the right part of FIG. 5B to incline the object P in the raising direction, the single-action operation is performed that involves only operation of the bed actuation lever.

When the bed 6 once actuated in the normal rotation or reverse rotation is to be rotated in the reverse direction (such as when the bed is restored to the position shown by the dashed line in FIGS. 5A and 5B), the bed can be actuated in a single-action operation regardless of the rotational direction. For example, when the bed 6 is to be inclined in the direction indicated by the arrow A in the right part of FIG. 5B, as described above, the bed is actuated in the double-action operation that involves pressing of the reverse inclination permission switch and clockwise rotation of the bed actuation lever. On the other hand, when the inclined bed is to be actuated in the reverse direction to the arrow A and restored to the position shown by the dashed line (the horizontal rest position, for example), the reverse inclination permission switch does not have to be pressed, and the bed can be actuated in a single-action operation that involves rotating the bed actuation lever in the reverse direction to the direction shown in the upper left part of FIG. 5B, that is, rotating the bed actuation lever counterclockwise.

As described above, the X-ray diagnostic apparatus 100 according to this embodiment can switch the bed actuation in response to the orientation of the object P placed on the bed independently of the setting. In particular, it can be ensured that the double-action operation is performed when the bed 6 is reversely inclined in the direction of inverting the object P. In addition, the bed actuation can be automatically switched based on the determination of the orientation of the object P, and therefore, the bed can be more safely actuated. Even if the user is unaware of whether the object P is placed on the bed in the normal position or reverse position, the bed is actuated in the double-action operation when the bed is reversely inclined in the direction of inverting the object P, and in the single-action operation when the bed is inclined in the raising direction, so that the operability can be improved.

An example in which the determination of the examination mode is made based on the position of the foot rest 8 has been described above with reference to the flowchart of FIG. 4. Alternatively, however, the determination of the examination mode may be made based on the position of the shoulder rest 4, instead of the position of the foot rest 8. Furthermore, the determination may also be made based on the position of a device capable of determining the orientation of the object P placed on the bed, such as an electrocardiograph.

Alternatively, the determination of the examination mode may be made based on the type of the examination or the part to be examined, instead of the position of the shoulder rest 4, the foot rest 8 or the like. For example, in a case of an examination or surgery of the head, various devices are disposed around the head, and the doctors or other practitioners are positioned around the head. On the other hand, in a case of an examination or surgery of a lower limb, the devices or practitioners are positioned around the legs. That is, the orientation of the patient placed on the bed can vary with the part to be examined so that the part to be examined is located at a position where a wide space is provided for the devices or practitioners. In addition, since the devices used vary with the type of the examination, the orientation of the patient placed on the bed 6 can vary with the type of the examination. The determination function 225 can obtain information on the part to be examined or the type of the examination from the HIS/RIS 200 and determine the examination mode is the normal position mode or the reverse position mode.

Furthermore, the examination mode can also be determined by determining the orientation of the patient placed on the bed 6 based on the type of the examination or the part to be examined as well as the range of movement of the bed 6 described later or the like.

Furthermore, the correspondence between the type of the examination or the part to be examined and the examination mode may be previously set or may be able to be individually set for each apparatus or hospital.

Furthermore, an alarm may be displayed on the display 34 when the examination mode determined based on the part to be examined or the type of the examination and the examination mode determined based on the position of the shoulder rest 4, the foot rest 8 or the like disagree. Such a check can reduce a perception gap between the doctor or the like who requests for the examination and the practitioner or the like who performs the examination, the possibility of an erroneous setting or the like.

Furthermore, the determination of the examination mode is not exclusively made by the determination function 225. For example, the console 30 may be configured to accept a choice of the normal position mode or the reverse position mode, and a choice of whether the head of the object is located closer to one shorter side of the bed 6 or closer to another shorter side of the bed 6 may be made through operation of the input device 35 by the practitioner.

In the above embodiment, an example has been described where whether the bed is actuated in a single-action operation or a double-action operation depends on the examination mode. However, the operation that can be switched depending on the examination mode is not limited to the bed actuation. For example, the range of movement of the bed, the horizontal rest position of the bed, or the speed of movement of the bed can also be changed depending on the examination mode.

The range of movement of the bed 6 is determined by a limit position of rotation of the bed 6 in the direction of raising the object P and a limit position of rotation of the bed 6 in the direction of inverting the object P. The operation performed to actuate the bed varies depending on the limit positions. For example, the angle of rotation of the bed in the direction of raising the object P can be greater than the angle of rotation of the bed in the direction of inverting the object P. The horizontal rest position is the initial position of the bed 6. The initial position of the bed 6 is usually not perfectly parallel with the floor surface (installation surface). For example, if the object P is placed on the bed 6 in a perfectly horizontal position, the object P (patient) feels as if the object P is slightly inclined with the head down. Therefore, when the X-ray diagnostic apparatus 100 is installed, a position in which the object P is slightly inclined with the head up is set as the horizontal rest position. In addition, depending on the safety of the bed actuation, the usability of the X-ray diagnostic apparatus 100 or the like, the speed of movement of the bed differs between the directions of movement. For example, the speed of movement in the inverting direction can be lower than the speed of movement in the raising direction.

As described above, with the X-ray diagnostic apparatus 100 according to this embodiment, the operation, setting or the like that differs between the raising direction and the inverting direction can also be changed depending on the examination mode.

Figure 6:
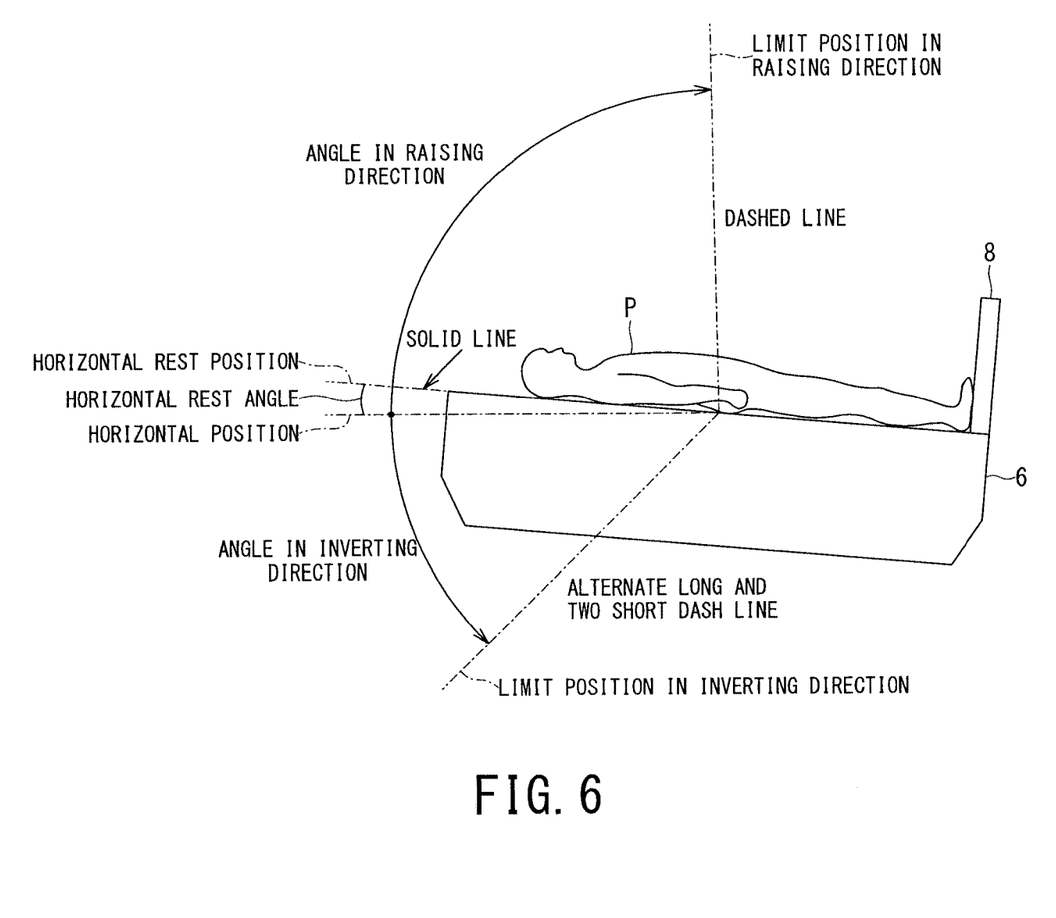
FIG. 6 is a diagram for illustrating a range of movement of a bed and a horizontal rest position of the bed of the X-ray diagnostic apparatus according to the embodiment in the normal position mode.

FIG. 6 is a diagram for illustrating the range of movement of the bed and the horizontal rest position of the bed of the X-ray diagnostic apparatus 100 according to this embodiment in the normal position mode. The alternate short and long dash line in FIG. 6 indicates a horizontal position with respect to the floor surface. An actual initial position of the bed 6 is the horizontal rest position shown by the solid line in FIG. 6. The horizontal rest position of the bed 6 is a position that is rotated by a horizontal rest angle from the horizontal position in the raising direction. The position shown by the dashed line in FIG. 6 is a limit position in the raising direction, and the position shown by the alternate long and two short dash line is a limit position in the inverting direction. As shown in FIG. 6, the angle of rotation in the raising direction is set to be greater than the angle of rotation in the inverting direction.

With the conventional X-ray diagnostic apparatus, if the object P is placed in the reverse position, which is the position reverse to the position shown in FIG. 6, the object P will lie on the bed 6 with the head down in the horizontal rest position. In addition, the limit angle of rotation in the inverting direction is greater than the limit angle of rotation in the raising direction, and therefore, the examination that involves rotation of the bed in the raising direction is limited.

To the contrary, with the X-ray diagnostic apparatus 100 according to this embodiment, the horizontal rest position can be reversed depending on the examination mode, and the limit position in the raising direction and the limit position in the inverting direction can be reversed depending on the examination mode.

Figure 7:
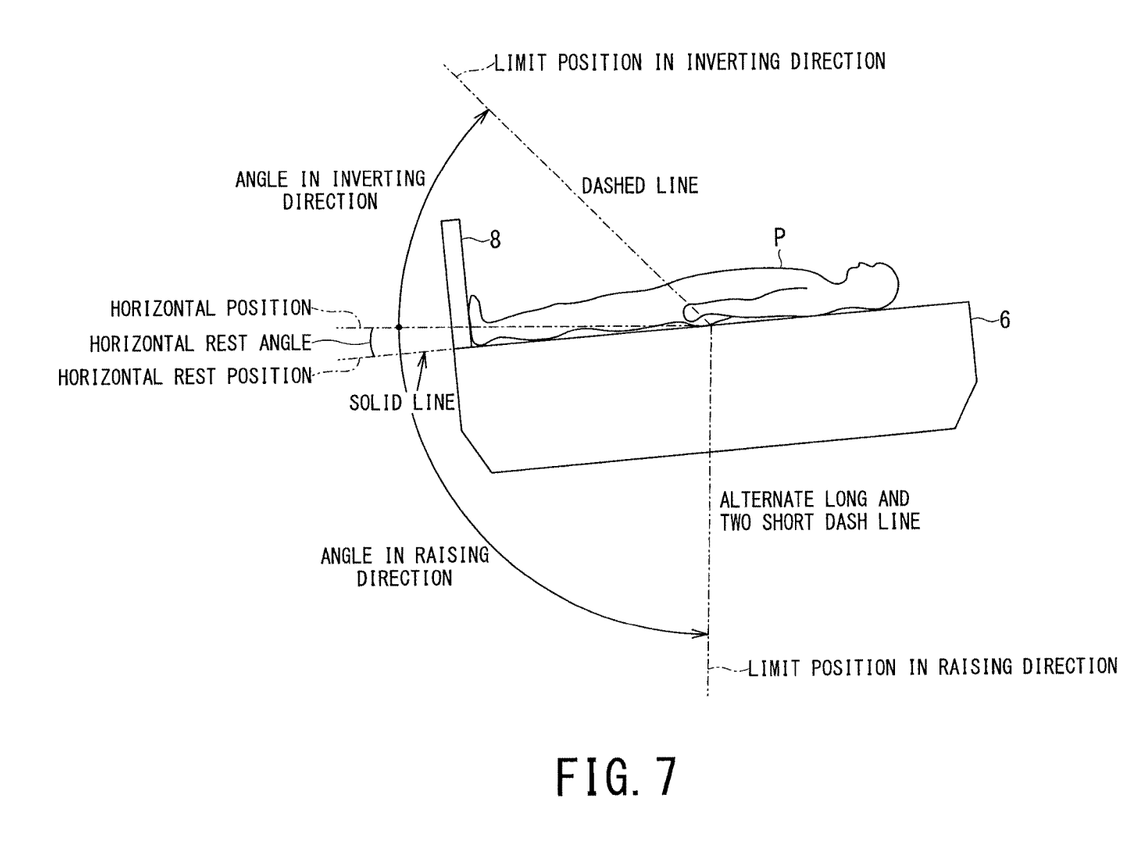
FIG. 7 is a diagram for illustrating a range of movement of the bed and a horizontal rest position of the bed of the X-ray diagnostic apparatus according to the embodiment in the reverse position mode.

FIG. 7 is a diagram for illustrating the range of movement of the bed and the horizontal rest position of the X-ray diagnostic apparatus 100 according to this embodiment in the reverse position mode. If the determination function 225 determines that the examination mode is the reverse headto-foot position mode, the bed control function 227 reverses the horizontal rest position of the bed, the limit position in the raising direction of the bed and the limit position in the inverting direction of the bed with respect to those in the normal position mode as shown in FIG. 7. In FIG. 7, the limit position in the raising direction and the limit position in the inverting direction are reversed with respect to those shown in FIG. 6, and the angle of rotation in the raising direction is set to be greater than the angle of rotation in the inverting direction. In addition, since the limit position in the raising direction is reversed, the horizontal rest position is set at a position rotated in the raising direction from the horizontal position.

As described above, settings of the horizontal rest position, the range of movement and the speed of movement can be changed depending on the examination mode, and therefore, the examination in the reverse position mode can be performed with the same settings as those of the examination in the normal position mode. Therefore, settings do not have to be changed for the reverse position mode in each examination, and the examination in the reverse position mode can be easily performed.

Furthermore, a plurality of limit positions in the inverting direction may be set at certain angular intervals, and the bed actuation may vary with the limit positions. For example, when the bed is to be inclined from the horizontal rest position in the inverting direction, a position rotated by a predetermined angle from the horizontal rest position may be defined as a first limit position in the inverting direction, the reverse inclination from the horizontal rest position to the first limit position in the inverting direction may be achieved in a double-action operation, and a further reverse inclination from the first limit position in the inverting direction may be achieved in a single-action operation. When the bed is reversely inclined in the direction of inverting the object P, there is a possibility that the object P falls headlong off the bed as described above, and therefore, the double-action operation is required in order to avoid the accident and improve the safety. On the other hand, once the reverse inclination is started, the problem of the safety from accidental actuation of the bed is less important than the problem of the operability for the user who has to operate the bed actuation lever while pressing the reverse inclination permission switch. Therefore, after the bed is rotated beyond a predetermined angle, a limit position at which the bed can be actuated in a single-action operation can be set.

Furthermore, a limit position may be set at a position where the bed is further inverted from the limit position in the inverting direction shown in FIG. 6. For example, the limit position in the inverting direction may be set at a position 180 degrees opposite to the limit position in the raising direction. The position 180 degrees opposite to the limit position in the raising direction may be defined as a second limit position in the inverting direction, and the reverse inclination of the bed in the direction toward the second limit position in the inverting direction from the limit position in the inverting direction shown in FIG. 6 may be achieved in a double-action operation. When the bed is reversely inclined in the direction toward the second limit position in the inverting direction from the limit position in the inverting direction shown in FIG. 6, the object P is in an almost inverted position, and therefore, a measure such as fastening the object P with a belt or the like needs to be taken to prevent the object P from falling off the bed. From the viewpoint of safety, such an actuation of the bed may be achieved in a double-action operation.

The operation of restoring the inclined bed 6 to the horizontal rest position may be achieved in a single-action operation. In this way, various settings can be changed depending on whether the examination mode is the normal head-to-foot position mode or the reverse head-to-foot position mode.

Furthermore, the orientation of the image displayed on the display 34 or the imaging position input through the input device 35 can also be changed depending on the examination mode.

Figure 8A:
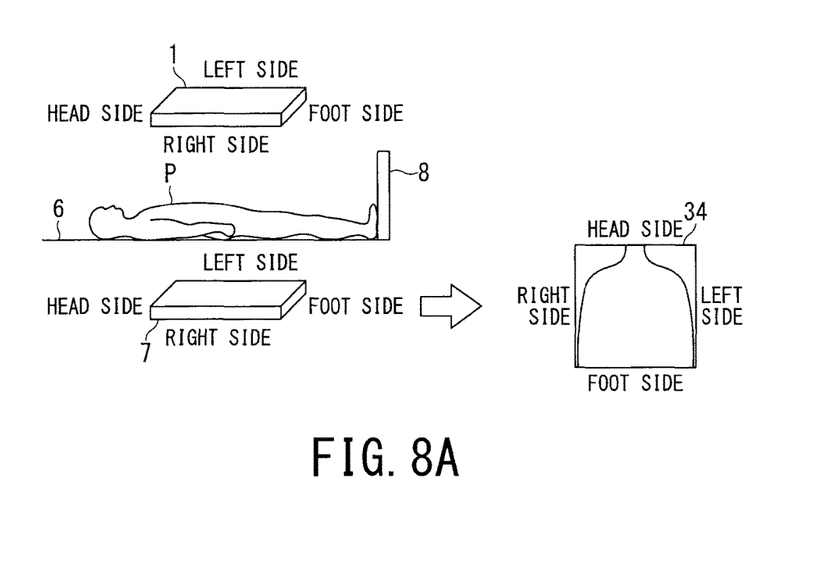
FIG. 8A is a diagram for illustrating an imaging orientation of the X-ray diagnostic apparatus according to the embodiment and an orientation of an X-ray image.
Figure 8B:
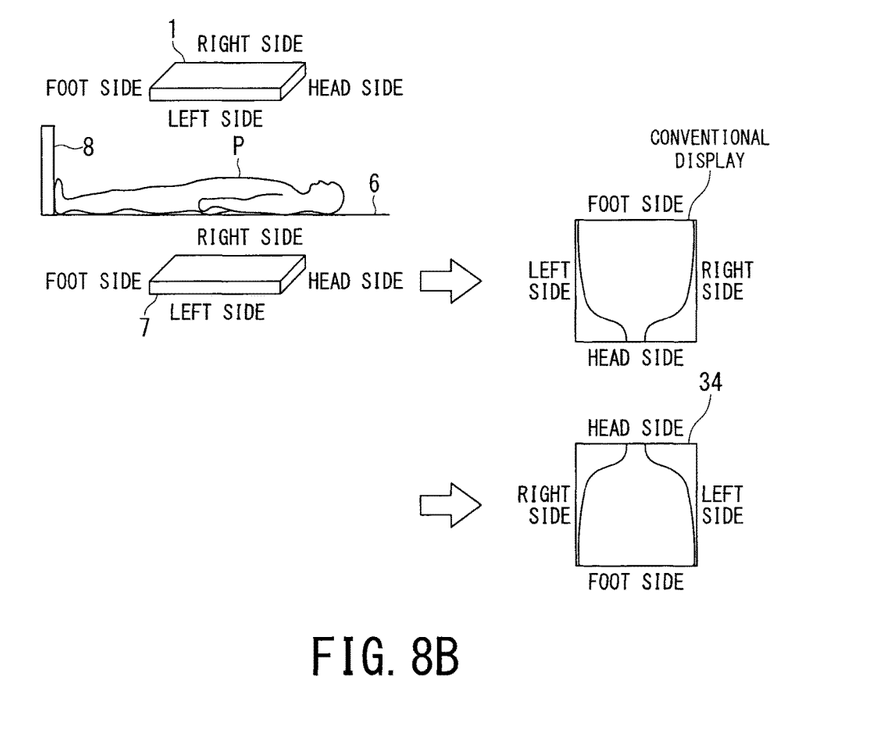
FIG. 8B is a diagram for illustrating an imaging orientation of the X-ray diagnostic apparatus according to the embodiment and orientations of X-ray images.

FIGS. 8A and 8B are diagrams for illustrating imaging orientations of the X-ray diagnostic apparatus 100 according to this embodiment and orientations of X-ray images. FIG. 8A shows an example of the orientations of the imaging unit 1, the X-ray detecting unit 7 and the display 34 in the case where the object is placed on the bed 6 in the normal position. FIG. 8B shows an example of the orientations of the imaging unit 1, the X-ray detecting unit 7 and the display 34 in the case where the object is placed on the bed 6 in the reverse position.

In FIGS. 8A and 8B, a head side, a foot side, a right side and a left side of the object P are shown for each of the imaging unit 1, the X-ray detecting unit 7, and the display 34. In the case of the normal position orientation shown in FIG. 8A, the upper side of a screen of the display 34 on which the image is displayed corresponds to the head side of the object P, the lower side of the screen corresponds to the foot side of the object P, the right side of the screen corresponds to the left side of the object P, and the left side of the screen corresponds to the right side of the object P. In the case of the reverse position orientation shown in FIG. 8B, in a conventional display shown in the upper right part of FIG. 8B, the upper side of the screen of the display section corresponds to the foot side of the object P, the lower side of the screen corresponds to the head side of the object P, the right side of the screen corresponds to the right side of the object P, and the left side of the screen corresponds to the left side of the object P. Therefore, with the conventional X-ray diagnostic apparatus, the display on the display is changed by an input operation on an input device, such as vertical inversion or horizontal inversion.

With the X-ray diagnostic apparatus 100 according to this embodiment, even in the case where the object P is placed on the bed 6 in the reverse head-to-foot position, the examination mode can be determined, and the X-ray image can be automatically inverted for display on the display 34 if the examination mode is the reverse position mode, as shown in the lower right part of FIG. 8B. Therefore, the image inversion operation is not necessary, and the, image can be displayed on the display 34 in such a manner that the upper side of the screen corresponds to the head side of the object P, the lower side of the screen corresponds to the foot side of the object P, the right side of the screen corresponds to the left side of the object P, and the left side of the screen corresponds to the right side of the object P.

Furthermore, not only the display on the display 34 but also the direction of movement of the imaging unit 1 can be reversed. For example, when the imaging orientation is to be changed by moving the imaging unit 1 while observing the X-ray image, opposite imaging orientations have to be input in the cases shown in FIGS. 8A and 8B. With the conventional X-ray diagnostic apparatus, the control of the movement of the imaging unit is previously programmed in the console 30 or the input device 35, and therefore, the direction to be input may be the reverse direction to the direction in the display 34, depending on the orientation of the object placed on the bed. For example, the direction in which the imaging unit 1 is moved toward the head side in FIG. 8A corresponds to the direction in which the imaging unit 1 is moved toward the foot side in FIG. 8B.

With the X-ray diagnostic apparatus 100 according to this embodiment, if an operation of moving the imaging unit 1 toward the head side is instructed through an input operation on the input device 35 or the like based on the examination mode, the moving unit 1 can be controlled to move toward the head side regardless of whether the object is placed on the bed in the normal position or the reverse position. That is, the input operation on the input device 35 to cause a change of the imaging position is not changed, although the direction in which the imaging unit 1 is actually moved under the control of the imaging control function 221 in response to the input operation can be reversed depending on the examination mode.

As described above, with the X-ray diagnostic apparatus 100 according to this embodiment, the control of the movement of the imaging unit 1 programmed in the console 30 or the input device 35 is switched depending on the examination mode, and therefore, the bed can be actuated and imaging can be performed independently of the orientation of the object based on the determined examination mode.

The term "processor" used in the above description means a circuit such as a dedicated or general-purpose central processing unit (CPU) arithmetic circuit (circuitry), an application specific integrated circuit (ASIC), or a programmable logic device (for example, a simple programmable logic device (SPLD), a complex programmable logic device (CPLD), or a field programmable gate array (FPGA)). As an example, FIG. 1 shows a case where one processor is used in the first processing circuitry 22, and one processor is used in the second processing circuitry 32. Alternatively, however, two or more processors may be used in the first processing circuitry 22, and two or more processors may be used in the second processing circuitry 32.

The processors used in the first processing circuitry 22 and the second processing circuitry 32 read a program stored in the first storage circuitry 23 and the second storage circuitry 31, respectively, or read a program directly incorporated into a circuit of the processors and execute the program to implement a corresponding function. When a plurality of processors are used in the first processing circuitry 22 or the second processing circuitry 32, the first storage circuitry 23 or the second storage circuitry 31 that stores a program may be provided for each processor, or the single first storage circuitry 23 or the single second storage circuitry 31 shown in FIG. 1 may store the programs corresponding to the functions of the processors.

Although various functions, such as the imaging control function 221, the position detection function 223, the determination function 225 and the bed control function 227, and various controls of the display of images have been described above as being implemented by processors as an example, those functions and controls are not exclusively implemented by the first processing circuitry 22 or the second processing circuitry 32. All the functions or controls may also be performed by one of the first processing circuitry 22 and the second processing circuitry 32.

Although an embodiment of the present invention has been described above, this embodiment is given as an example and is not intended to limit the scope of the present invention. This embodiment can be implemented in other various forms, and various omissions, replacements or modifications can be made without departing from the spirit of the present invention. The embodiment and various modifications thereof are included in the scope and spirit of the present invention and are also included in the invention set forth in the claims and equivalents thereof.

What is claimed is:

1. An X-ray diagnostic apparatus, comprising:
a bed configured to have an object placed thereon;
a console configured to accept an operation to set one of two tilting directions of the bed; and
processing circuitry configured to
recognize a placed direction of the placed object from among two opposite directions along a longitudinal axis of the bed,
determine, based on the recognized placed direction, whether a set direction of the two tilting directions set using the console is an inverting direction or a raising direction, the inverting direction being defined as a direction in which the object is inclined to locate a head lower than a foot, and the raising direction being defined as a direction in which the object is inclined to locate the head higher than the foot, and
perform different control depending on whether the set direction set using the console is the inverting direction or the raising direction,
wherein the processing circuitry is further configured to determine, based on an examination mode including a normal direction mode or a reverse direction mode, whether the set direction is the inverting direction or the raising direction, the normal direction mode being a mode in which the placed direction is a positive direction of the two opposite directions, the reverse direction mode being a mode in which the placed direction is a negative direction of the two opposite directions.

2. The X-ray diagnostic apparatus according to claim 1, wherein the processing circuitry is further configured to recognize the placed direction, based on at least one of a position of a foot rest attached to the bed, a position of a shoulder rest attached to the bed, an examination type, and a region to be examined.

3. The X-ray diagnostic apparatus according to claim 1, wherein the console is further configured to accept input of the placed direction.

4. The X-ray diagnostic apparatus according to claim 1, wherein the processing circuitry is further configured to reverse, when the examination mode is the reverse direction mode, a range of movement of the bed, a horizontal rest position of the bed, and a speed of movement of the bed to a control when the examination mode is the normal direction mode.

5. The X-ray diagnostic apparatus according to claim 1, further comprising:
a display configured to display the an indication of the examination mode.

6. The X-ray diagnostic apparatus according to claim 5, wherein the display displays an X-ray image of the object placed on the bed and changes a display orientation so as to make a head side of the object in the X-ray image agree with an upper side of a screen of the display.

7. The X-ray diagnostic apparatus according to claim 1, further comprising:
an imaging device configured to produce an X-ray used to image the object; and
an input device included in the console and configured to input a direction of movement of the imaging device,
wherein the processing circuitry is further configured to control a movement of the imaging device in response to the examination mode.

8. An X-ray diagnostic apparatus, comprising:
a bed configured to have an object placed thereon;
a console configured to accept an operation to set one of two tilting directions of the bed; and
processing circuitry configured to
- recognize a placed direction of the placed object from among two opposite directions along a longitudinal axis of the bed,
- determine, based on the recognized placed direction, whether a set direction of the two tilting directions set using the console is an inverting direction or a raising direction, the inverting direction being defined as a direction in which the object is inclined to locate a head lower than a foot, and the raising direction being defined as a direction in which the object is inclined to locate the head higher than the foot, and
- perform different control depending on whether the set direction set using the console is the inverting direction or the raising direction,
- wherein the processing circuitry is further configured to
  - perform a control such that an operation in the set direction corresponds to a single-action operation when the set direction is determined as the raising direction, and perform a control such that an operation in the set direction corresponds to a double-action operation when the set direction is determined as the inverting direction.

9. The X-ray diagnostic apparatus according to claim 8, wherein the processing circuitry is further configured to recognize the placed direction, based on at least one of a position of a foot rest attached to the bed, a position of a shoulder rest attached to the bed, an examination type, and a region to be examined.

10. The X-ray diagnostic apparatus according to claim 8, wherein the console is further configured to accept input of the placed direction.

\* \* \* \* \*